(12) United States Patent
Sayo et al.

(10) Patent No.: US 6,313,317 B1
(45) Date of Patent: Nov. 6, 2001

(54) RUTHENIUM-PHOSPHINE COMPLEX AND METHOD FOR PRODUCING THE SAME

(75) Inventors: Noboru Sayo; Takao Saito; Tohru Yokozawa, all of Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/273,260

(22) Filed: Mar. 22, 1999

(30) Foreign Application Priority Data

Mar. 23, 1998 (JP) .................................................. 10-092174

(51) Int. Cl.$^7$ .............................. C07F 9/30; C07D 317/50
(52) U.S. Cl. ........................ 549/220; 549/221; 549/435; 502/164; 502/230; 502/326
(58) Field of Search .................................. 502/164, 230, 502/326; 549/435, 220, 221

(56) References Cited

U.S. PATENT DOCUMENTS 5,872,273 * 2/1999 Saito et al. .

OTHER PUBLICATIONS

Ohta et al., "An Anionic Dinuclear BINAP–Ruthenium(II) Complex: Crystal Structure . . . " *Organometallics*, vol. 15, No. 6, 1996, pp. 1521–1523.

Ikariya et al., "Synthesis of Novel Chiral Ruthenium Complexes of 2,2'. . . ", *J. Chem. Soc., Chem. Commun.*, 1985, pp. 922–924.

Kawano et al., "Aysmmetric Hydrogenation of Prochiral Alkenes Catalysed . . . ", *J. Chem. Soc. Perkin Trans. I*, 1989, pp. 1571–1575.

Patent Abstract of Japan Publication; No. 10–182678, Publication Date Jul. 7, 1998.

* cited by examiner

Primary Examiner—T. A. Solola
(74) Attorney, Agent, or Firm—Kubovcik & Kubovcik

(57) ABSTRACT

Disclosed is a ruthenium-phosphine complex usable as the catalyst giving a high enantiomer excess in an asymmetric reaction and a method for producing the complex. The ruthenium-phosphine complex is represented by formula (1):

$$[\{(RuX(L)\}_2(\mu\text{-}X)_3]^-[R^2{}_2NH_2]^+ \qquad (1)$$

wherein $R^2$ represents hydrogen, alkyl, cycloalkyl or benzyl and L represents a diphosphine ligand represented by formula (2):

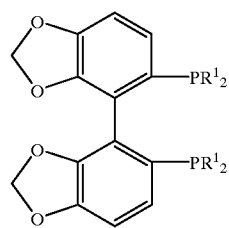

(2)

wherein $R^1$ represents an optionally substituted phenyl group and X represents a halogen atom. The method for preparing a ruthenium-phosphine complex represented by formula (1) is characterized in that a ruthenium complex represented by the formula [RuX(arene)(L)]X and an ammonium salt represented by the formula $R^2{}_2$NH.HX are reacted with each other.

2 Claims, No Drawings

RUTHENIUM-PHOSPHINE COMPLEX AND METHOD FOR PRODUCING THE SAME

BACKGROUND OF THE INVENTION

1. Field of the Invention

The present invention relates to a novel ruthenium-phosphine complex represented by the following general formula (1) and to an asymmetric hydrogenation catalyst comprising the complex.

$$[\{RuX(L)\}_2(\mu\text{-}X)_3]^-[R^2{}_2NH_2]^+ \quad (1)$$

2. Description of Prior Art

Many organic synthetic reactions using a transition metal complex as the catalyst have been developed and exploited to achieve various objects. In particular, there have been many reports concerning asymmetric catalysts used in an asymmetric hydrogenation reaction. There have been many studies in which complexes comprising a transition metal atom and an optically active phosphine are used as an asymmetric hydrogenation catalyst since a report was made that a complex containing, as the ligands, a rhodium atom and an optically active phosphine was selectively used as an asymmetric hydrogenation catalyst to prepare an optically active compound with high enantiomer excess.

For example, in J. Chem. Soc., Chem. Commun. (1985), 922 and J. Chem. Soc., Perkin Trans. I, (1987), 1571, technologies are disclosed in which an acylaminoacrylic acid derivative is hydrogenated using 2,2'-bis(diphenylphosphine)-1,1'-binaphthyl-ruthenium complex $(Ru_2Cl_4(BINAP)_2 \cdot Et_3N$, which is hereinafter called "BINAP-Ru complex") to produce an optically active amino acid derivative.

Recently, a ruthenium complex of p-MeO-BINAP, namely, $[\{RuCl(p\text{-}MeO\text{-}BINAP)\}_2 (\mu\text{-}Cl)_3]^-[Et_2NH_2]^+$ has been disclosed in Organometallics, 15 (1996), 1521. Moreover, Japanese Patent Application No. 8-359818 discloses an asymmetric hydrogenation reaction of ketones by using ((5,6), (5', 6')-bis(methylenedioxy)biphenyl-2,2'-diyl)bis(diphenylphosphine)-ruthenium complex (hereinafter called "SEGPHOS-Ru complex").

However, the ruthenium complexes used in Japanese Patent Application No. 8-359818, for example, are complicated in the preparation of the complexes, have a problem in stability and yield and production of complicated mixtures. These complexes also have insufficient catalytic activity and durability.

Ruthenium metals are relatively inexpensive among transition metals and are expected to serve as an industrially advantageous catalyst. These catalysts, however, have unsolved problems in the preciseness and application of reaction. Hence there is a demand for catalysts which can be easily produced, are inexpensive, have a high activity and durability, and can give a enantiomer excess in an asymmetric reaction, making products of optically high purity.

SUMMARY OF THE INVENTION

The inventors of the present invention have conducted earnest studies in response to such a demand, and, as a result, have found a novel ruthenium complex which can be used as a common synthetic catalyst when an optically inactive material is used as the ligand in the complex and in turn as an asymmetric synthetic catalyst when an optically active material is used as the ligand and which has high catalytic activity, the objective complex being obtained in a high yield in a simple operation. The present invention has thus been completed.

1. Thus the present invention provides a ruthenium-phosphine complex represented by the general formula (1):

$$[\{RuX(L)\}_2(\mu\text{-}X)_3]^-[R^2{}_2NH_2]^+ \quad (1)$$

wherein $R^2$ represents a hydrogen atom, an alkyl group having 1–4 carbon atoms, a cycloalkyl group having 3–8 carbon atoms, a phenyl group or a benzyl group and L represents a diphosphine ligand represented by the general formula (2):

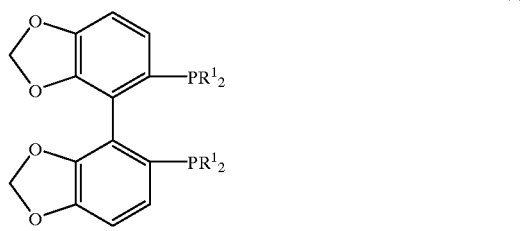

(2)

wherein $R^1$ represents a phenyl group which is optionally substituted with up to three substituents selected from alkyl of 1–4 carbon atoms, alkoxy of 1–4 carbon atoms, methylenedioxy, halogen, halomethyl, cycloalkyl of 3–8 carbon atoms, 1-naphthyl and 2-naphthyl, and X represents a halogen atom.

2. The present invention further provides a method for preparing a ruthenium-phosphine complex, said method comprising reacting a ruthenium complex represented by the general formula (3):

$$[RuX(arene)(L)]X \quad (3)$$

wherein X represents a halogen atom, arene represents a phenyl group which is optionally substituted with up to six substituents selected from alkyl of 1–3 carbon atoms, alkoxycarbonyl of 1–2 carbon atoms and halogen and L represents a tertiary diphosphine ligand represented by the general formula (2):

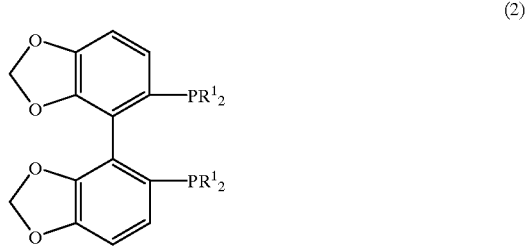

(2)

wherein $R^1$ represents a phenyl group which is optionally substituted with up to three substituents selected from alkyl of 1–4 carbon atoms, alkoxy of 1–4 carbon atoms, methylenedioxy, halogen, trihalomethyl, cycloalkyl of 3–8 carbon atoms, 1-naphthyl and 2-naphthyl, with an ammonium salt represented by the general formula (4)

$$R^2{}_2NH \cdot HX \quad (4)$$

wherein $R^2$ represents a hydrogen atom, an alkyl group having 1–4 carbon atoms, a cycloalkyl group having 3–8 carbon atoms, a phenyl group or a benzyl group and X represents a halogen atom, to produce a ruthenium-phosphine complex represented by the general formula (1):

$$[\{RuX(L)\}_2(\mu\text{-}X)_3]^-[R^2{}_2NH_2]^+ \quad (1)$$

wherein R², L and X are the same as defined above.

3. The present invention further provides a method for preparing a ruthenium-phosphine complex, said method comprising reacting a ruthenium complex represented by the general formula (5):

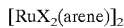  (5)

wherein X represents a halogen atom and arene represents a phenyl group which is optionally substituted with up to six substituents selected from alkyl of 1–3 carbon atoms, alkoxycarbonyl of 1–2 carbon atoms and halogen, with a tertiary diphosphine ligand represented by the general formula (2):

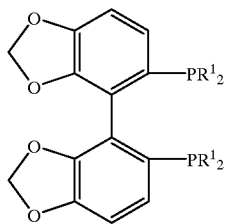  (2)

wherein $R^1$ represents a phenyl group which is optionally substituted with up to three substituents selected from alkyl of 1–4 carbon atoms, alkoxy of 1–4 carbon atoms, methylenedioxy, halogen, trihalomethyl, cycloalkyl of 3–8 carbon atoms, 1-naphthyl and 2-naphthyl, and an ammonium salt represented by the general formula (4):

  (4)

wherein $R^2$ represents a hydrogen atom, an alkyl group having 1–4 carbon atoms, a cycloalkyl group having 3–8 carbon atoms, a phenyl group or a benzyl group and X represents a halogen atom, to produce a ruthenium-phosphine complex represented by the general formula (1):

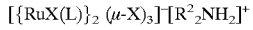  (1)

4. According to the present invention, there is also provided an asymmetric hydrogenation catalyst comprising the aforementioned ruthenium-phosphine complex, the catalyst being used to produce allyl alcohols, olefin acids or ketones.

DETAILED DESCRIPTION OF THE INVENTION

The invention will be explained in detail.

The novel ruthenium-phosphine complex of the present invention is, as aforementioned, a compound represented by the general formula (1):

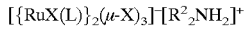  (1)

Specific examples of the tertiary diphosphine represented by L in the above general formula (1) include (5,6), (5',6')-bis(methylenedioxy)biphenyl-2,2'-diyl-bis(diphenylphosphine) (hereinafter abbreviated as "SEGPHOS") containing a phenyl group as $R^1$ in the general formula (2):

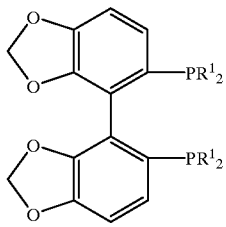  (2)

and phosphine compounds containing as $R^1$, a 4-methylphenyl group, 4-tert-butylphenyl group, 3-methylphenyl group, 3,5-dimethylphenyl group, 3,5-ditert-butylphenyl group, 4-chlorophenyl group, 4-fluorophenyl group, 4-trifluoromethylphenyl group, 4-methoxyphenyl group, 3,5-dimethoxyphenyl group, 3,4-methylenedioxyphenyl group, 3,5-dimethyl-4-methoxyphenyl group, 3,5-ditert-butyl-4-methoxyphenyl group, 2-naphthyl group, 1-naphthyl group, cyclohexyl group or cyclopentyl group. Preferred examples are phosphine compounds containing a phenyl group, 4-methylphenyl group, 4-tert-butylphenyl group, 3,5-dimethylphenyl group, 3,5-dimethyl-4-methoxyphenyl group, 3,5-ditert-butylphenyl group, cyclohexyl group or the like. As examples of X in the general formula (1), a chlorine atom, bromine atom and iodine atom are given.

Such a ruthenium-phosphine complex represented by the general formula (1) in the present invention can be prepared by the aforementioned two methods (the above methods 2 and 3). The preparative method makes it possible to produce the complex as a pure and single product through a process which does not require refining such as crystallization.

Examples of the arene in the general formula (3) include benzene, toluene, xylene, mesitylene, p-cymene, cumene, hexamethylbenzene, ethylbenzene, methyl benzoate, ethyl benzoate, anisole, chlorobenzene, dichlorobenzene, bromobenzene and fluorobenzene. Given as examples of X in the general formula (3) are a chlorine atom, bromine atom and iodine atom.

In the general formula (4), examples of $R^2$ include a phenyl group, a cyclohexyl group or a cyclopentyl group. X and the arene in the general formula (5) are the same as described above.

Among the compounds represented by the general formula (3) in the present invention, the ruthenium complex, [RuX(arene)(L)]X, containing a phenyl group as the arene which is optionally substituted may be produced as follows.

A ruthenium complex containing a chlorine atom as X, namely, [RuCl(arene)(L)]Cl, can be quantitatively synthesized using, for example, [RuCl₂(arene)]₂ prepared according to the method described in G Wikhaus, J. Org. Chem., 41 (1976), 487 or R. A. Zelonka, Can. J. Chem., 50 (1972), 3643, as a starting material. Specifically, this material is reacted with tertiary diphosphine L at 20 to 50° C. for 1 to 3 hours in a solvent such as methanol, ethanol, benzene, or methylene chloride or in a mixture of these solvents and the solvent is then distilled under reduced pressure to produce the ruthenium complex.

When a ruthenium complex containing a bromine or iodine atom as X, namely, [RuBr(arene)(L)]Br or [RuI(arene)(L)]I is produced, for example, [RuCl₂(arene)]₂ is first used as a starting material. This material is reacted with a salt represented by the formula (6) in water used as the solvent:

  (6)

wherein $M^1$ represents an alkali metal such as Li, Na or K and Z represents Br or I. Alternatively, $[RuCl_2(arene)]_2$ and $M^1Z$ are mixed and stirred at room temperature in a mixture of methylene chloride and water used as the solvent by using as a phase transfer catalyst a quaternary ammonium salt or a quaternary phosphonium salt represented by the following formula (7) to obtain $[RuZ_2 (arene)]_2$:

$$R^4R^5R^6R^7 QX^1 \tag{7}$$

wherein $R^4, R^5, R^6$ and $R^7$ respectively represent an alkyl group having 1–16 carbon atoms, a phenyl group or a benzyl group, Q represents a nitrogen atom or a phosphorus atom and $X^1$ represents a halogen atom.

As the phase transfer catalyst, for example, compounds described in W. P. Weber and G. W. Gokel (translated by Iwao Tabushi and Takako Nishitani): Phase Transfer Catalyst, Kagaku Dojin (1978) may be used. Specific examples of compounds usable as the phase transfer catalyst include $Et_4NCl$, $Et_4NBr$, $Et_4NI$, $Bu_4NCl$, $Bu_4NBr$, $Bu_4NI$, (Benzyl)$Et_3NCl$, (Benzyl)$Et_3NBr$, (Benzyl) $Et_3NI$, (Benzyl) $Pr_3NCl$, (Benzyl) $Pr_3NBr$, (Benzyl) $Pr_3NI$, $(C_8H_{17})Me_3NCl$, $(C_8H_{17})Me_3NBr$, $(C_8H_{17})Me_3NI$, $(C_{16}H_{33})Me_3NCl$, $(C_{16}H_{33})Me_3NBr$, $(C_{16}H_{33})Me_3NI$, $MePh_3PCl$, $MePh_3PBr$, $MePh_3PI$, $EtPh_3PCl$, $EtPh_3PBr$, $EtPh_3PI$, $BuPh_3PCl$, $BuPh_3PBr$, $BuPh_3PI$, $(C_8H_{17})Ph_3PCl$, $(C_8H_{17})$ $Ph_3PBr$, $(C_8H_{17})$ $Ph_3PI$, $(C_{16}H_{33})Ph_3PCl$, $(C_{16}H_{33})$ $Ph_3PBr$, $(C_{16}H_{33})$ $Ph_3PI$, $(C_{16}H_{33})$ $Bu_3PCl$, $(C_{16}H_{33})$ $BU_3PBr$ and $(C_{16}H_{33})$ $Bu_3PI$.

Then the resulting $[RuZ_2(arene)]_2$ is reacted with tertiary diphosphine L at 20° C. to 50° C. for 1 to 3 hours in a solvent such as methanol, ethanol, benzene or methylene chloride or a mixture of these solvents, followed by distilling the solvent under reduced pressure, to synthesize $[RuBr(arene)(L)]Br$ or $[RuI(arene)(L)]I$ quantitatively.

Using $[RuX(arene) (L)]X$ obtained in this manner as an intermediate, for example, $[\{RuCl(SEGPHOS)\}_2(\mu\text{-}Cl)_3]^-[Et_2NH_2]^+$ may be produced by the following method.

Specifically, a $[RuCl(benzene) (SEGPHOS)]Cl$ complex is reacted with $Et_2NH.HCl$ at 50 to 100° C. for 5 to 20 hours in a solvent such as benzene, toluene, xylene, tetrahydrofuran (THF), dioxane, dimethoxyethane (DME), dimethylformamide (DMF), dimethylacetamide (DMA) or dioxolan, followed by distilling the solvent under reduced pressure, to synthesize $[\{RuCl(SEGPHOS)\}_2(\mu\text{-}Cl)_3]^-[Et_2NH_2]^+$ quantitatively.

Also, $[RuZ_2(arene)]_2$ used as an intermediate is reacted with, for example, SEGPHOS and $Et_2NH.HCl$ at 50 to 100° C. for 5 to 20 hours in a solvent such as benzene, toluene, xylene, tetrahydrofuran (THF), dioxane, dimethoxyethane (DME), dimethylformamide (DMF), dimethylacetamide (DMA) or dioxolan, followed by distilling the solvent under reduced pressure, to synthesize $[\{RuCl(SEGPHOS)\}_2(\mu\text{-}Cl)_3]^-[Et_2NH_2]^+$ quantitatively.

The ruthenium-phosphine complex of the present invention is thus synthesized as a pure and single product without refining. It was confirmed by $^{31}P$-NMR analysis or the like that the resulting ruthenium-phosphine complex of the present invention is a pure complex.

The ruthenium-phosphine complex of the present invention is stable and exhibits outstandingly high activity when it is used in an asymmetric hydrogenation reaction. Thus, for example, by using 1/100 to 1/10000 molar ratio to the substrate of the ruthenium-phosphine complex of the present invention, the reaction proceeds promptly with the result of high purity and optical purity of the hydrogenation products.

The ruthenium-phosphine complex of the present invention is particularly useful in the asymmetric hydrogenation of a compound (substrate) of the following general formula (8):

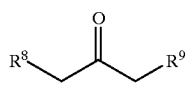

(8)

wherein $R^8$ represents a hydrogen atom, an alkyl group having 1–10 carbon atoms, halogen, an alkoxy group having 1–4 carbon atoms and a benzyloxy group and $R^9$ represents a hydroxy group, an alkoxycarbonyl group, where the alkoxy group has 1–4 carbon atoms, a benzyloxycarbonyl group, a hydroxymethyl group and a dialkylamino group, where the alkyl groups have 1–4 carbon atoms.

Examples of the substrate used in the asymmetric hydrogenation reaction include allyl alcohols such as geraniol and nerol, olefin acids such as α,β-unsaturated carboxylic acids, e.g., tiglic acid, dehydronaproxene and itaconic acid and ketones such as methyl acetoacetate, methyl 4-chloroacetoacetate, ethyl 2-oxo-4-phenyl butanoate, 2-oxopropanol and 2,4-pentanedione.

The novel ruthenium-phosphine complex according to the present invention is stable and exhibits markedly high activity when it is used as a catalyst for asymmetric hydrogenation of allyl alcohols, olefin acids or ketones with the result of high purity and optical purity of the hydrogenation products.

The production method of the present invention does not need refining and can synthesize a ruthenium-phosphine complex as a pure and single product.

EXAMPLES

The present invention will be explained in detail by way of the following examples which are not intended to be limiting of the present invention.

In the following examples, the properties of the compounds prepared in examples were measured using the following instruments.

| | |
|---|---|
| NMR | AM400 (manufactured by Bruker) |
| $^1H$-NMR | (400 MHz; internal standard: tetramethylsilane) |
| $^{31}P$-NMR | (162 MHz; internal standard: 85% phosphoric acid) |
| GLC | 5890-II (manufactured by Hewlett Packard) |

Example 1

Synthesis of $[\{RuCl((S)\text{-}SEGPHOS)\}_2(\mu\text{-}Cl)_3]^-[Et_2NH_2]^+$ $[RuCl_2(benzene)]_2$ (50 mg, 0.1 mmol) and (S)-SEGPHOS (122 mg, 0.2 mmol) were weighed and placed in a Schlenk tube, in which air was then replaced with nitrogen. After deaerated methylene chloride (5 ml) and ethanol (5 ml) were added, the mixture was stirred at 50° C. for 2 hours. The reaction solution was concentrated to obtain $[RuCl(benzene) ((S)\text{-}SEGPHOS)]Cl$ (0.17 g, yield:98%) as a brown solid.

$[RuCl(benzene)((S)\text{-}SEGPHOS)]Cl$ (0.17 g, 0.2 mmol) and dimethylamine hydrochloride (54 mg, 0.5 mmol) were weighed and placed in a Schlenk tube, in which air was then replaced with nitrogen. After deaerated 1,4-dioxane (20 ml) was added, the mixture was stirred under reflux for 16 hours. The reaction solution was concentrated to obtain the captioned compound (0.18 g, yield:98%) as a brown solid.

$^{31}$P-NMR(CDCl$_3$)δ; 51.24(d, J=39.0 Hz), 52.9 (d, J=39.1 Hz)

Example 2

Synthesis of [{RuCl((R)-SEGPHOS)}$_2$(μ-Cl) $_3$]$^-$ [Me$_2$NH$_2$]$^+$

[RuCl$_2$(benzene)]$_2$ (50 mg, 0.1 mmol),(R)-SEGPHOS (122 mg, 0.2 mmol) and dimethylamine hydrochloride (16 mg, 0.2 mmol) were weighed and placed in a Schlenk tube, in which air was then replaced with nitrogen. After deaerated THF (10 ml) was added, the mixture was stirred under reflux for 16 hours. The reaction solution was concentrated to obtain the captioned compound (0.16 g, yield:95%) as a brown solid.

$^{31}$P-NMR(CDCl$_3$)δ; 51.29(d, J=38.3 Hz), 51.72 (d, J=38.4 Hz)

Example 3

Asymmetric Hydrogenation Example No.1: Hydrogenation of 2-oxopropanol

[{RuCl((R)-SEGPHOS)}$_2$(μ-Cl)$_3$]$^-$[Me$_2$NH$_2$]$^+$(110.7 mg, 0.14 mmol) prepared in Example 2, 2-oxopropanol (101 g, 1.36 mol) and methanol (200 ml) were placed in a 1000 ml stainless autoclave and stirred at 65° C. under a hydrogen pressure of 30 atm for 8 hours. A measurement of the reaction solution by gas chromatography (GLC) showed that the conversion rate was 99.8%. Distillation of the reaction solution yielded 96.5 g of 1,2-dihydroxypropane (yield: 95.5%, enantiomer excess: 98%ee).

| GLC column | |
| --- | --- |
| Conversion rate: | FFAP 25 mx0.35 mm |
| | Inj. temp.: 220° C. |
| | Det. Temp.: 250° C. |
| Optical purity: | αDEX120 30 mx0.25 mm |
| | Inj. temp.: 220° C. |
| | Det. Temp.: 250° C. |

Comparative Example 1

Hydrogenation of 2-oxopropanol

[{RuCl((R)-BINAP)}$_2$(μ-Cl)$_3$]$^-$[Et$_2$NH$_2$]$^+$(11.4 mg, 6.8 mmol), 2-oxopropanol (2.0 g, 27 mmol) and methanol (6 ml) were placed in a 100 ml stainless autoclave and stirred at 54 °C. under a hydrogen pressure of 30 atm for 17 hours. A measurement of the reaction solution by GLC showed that the conversion rate was 100% and the enantiomer excess was 92.8%ee.

Examples 4–9

The same procedures as in Example 2 and in Example 1 were performed in Examples 4–6 and in Examples 7–9 respectively. The results are shown in Table 1.

TABLE 1

| Example | L | X | R$^2$ | $^{31}$PNMR (CDCl$_3$) δ |
| --- | --- | --- | --- | --- |
| 4 | Tol-SEGPHOS | Cl | Me | 49.80 (d, j = 38.5 Hz) |
| | | | | 5.026 (d, j = 39.0 Hz) |
| 5 | DM-SEGPHOS | Cl | Et | 51.31 (d, j = 42.0 Hz) |
| | | | | 54.84 (d, j = 41.0 Hz) |
| 6 | DMM-SEGPHOS | Cl | Et | 50.08 (d, j = 41.0 Hz) |
| | | | | 52.72 (d, j = 41.0 Hz) |
| 7 | SEGPHOS | Br | Et | 50.94 (d, j = 36.0 Hz) |
| | | | | 50.26 (d, j = 36.0 Hz) |
| 8 | SEGPHOS | Cl | i-Pr | 50.97 (d, j = 39.0 Hz) |
| | | | | 52.63 (d, j = 39.0 Hz) |
| 9 | t-Bu-SEGPHOS | Cl | Et | 49.96 (d, j = 39.0 Hz) |
| | | | | 50.21 (d, j = 41.0 Hz) |

(Note)
R$^1$ in L is shown by the following structural formulae.

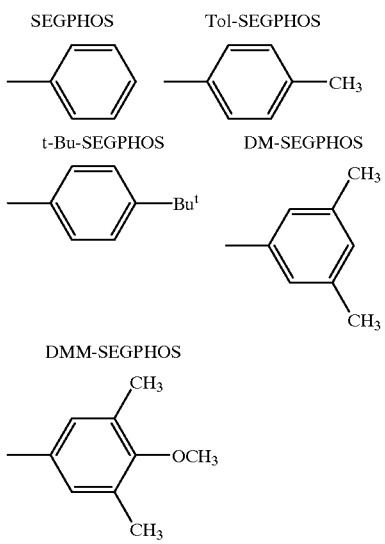

Example 10

Asymmetric Hydrogenation Example No. 2: Hydrogenation of ethyl 4-chloro-2-oxobutanoate

[{RuCl((R)-SEGPHOS)}$_2$ (μ-Cl)$_3$]$^-$[Me$_2$NH$_2$]$^+$(122.3 mg, 0.15 mmol) prepared in Example 2, ethyl 4-chloro-2-oxobutanoate (60.9 g, 0.37 mol) and ethanol (183 ml) were placed in a 500 ml stainless autoclave and stirred at 90° C. under a hydrogen pressure of 30 atm for 2 hours. A measurement of the reaction solution by GLC showed that the conversion rate was 99.8%. Distillation of the reaction solution yielded 54.6 g of ethyl (S)-4-chloro-2-oxobutanoate (yield: 88.5%, enantiomer excess: 98.5%ee).

| GLC column | |
| --- | --- |
| Conversion rate: | NEUTRA BOND-1 25 mx0.25 mm |
| | Inj. temp.: 230° C. |
| | Det. Temp.: 250° C. |
| Optical purity: | Chiraldex G-TA 30 mx0.25 mm |
| | Inj. temp.: 200° C. |
| | Det. Temp.: 200° C. |

Comparative Example 2

Hydrogenation of ethyl 4-chloro-2-oxobutanoate

Ethyl 4-chloro-2-oxobutanoate (3.29 g, 20 mmol), [{RuCl ((R)-BINAP) }$_2$(μ-Cl)$_3$]$^-$[Et$_2$NH$_2$]$^+$(6.8 mg, 4 mmol) and EtOH (5.4 ml) were stirred at 100° C. under a hydrogen pressure of 10 atm for 2 hours. The enantiomer yield measured was 95.3%ee.

What is claimed is:

1. A method for preparing a ruthenium-phosphine complex, said method comprising reacting a ruthenium complex of formula (3):

[RuX(arene)(L)]X  (3)

wherein X represents a halogen atom, arene represents a phenyl group which is optionally substituted with up to six substituents selected from alkyl of 1–3 carbon atoms, alkoxycarbonyl of 1–2 carbon atoms and halogen and L represents a tertiary diphosphine ligand of formula (2):

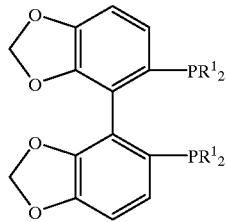

(2)

wherein $R^1$ represents a phenyl group which is optionally substituted with up to three substituents selected from alkyl of 1–4 carbon atoms, alkoxy of 1–4 carbon atoms, methylenedioxy, halogen, trihalomethyl, cycloalkyl of 3–8 carbon atoms, 1-naphthyl and 2-naphthyl, with an ammonium salt of formula (4):

$R^2_2$NH.HX  (4)

wherein $R^2$ represents a hydrogen atom, an alkyl group having 1–4 carbon atoms, a cycloalkyl group having 3–8 carbon atoms, a phenyl group or a benzyl group and X represents a halogen atom, to produce a ruthenium-phosphine complex of formula (1):

[{RuX(L)}$_2$($\mu$-X)$_3$]⁻[$R^2_2$NH$_2$]⁺  (1).

2. The method of claim 1, wherein a ruthenium complex of formula (5):

[RuX$_2$(arene)]$_2$  (5), wherein X represents a halogen atom and arene represents a phenyl group which is optionally substituted with up to six substituents selected from alkyl of 1–3 carbon atoms, alkoxycarbonyl of 1–2 carbon atoms and halogen, is reacted with a tertiary diphosphine ligand L of formula (2):

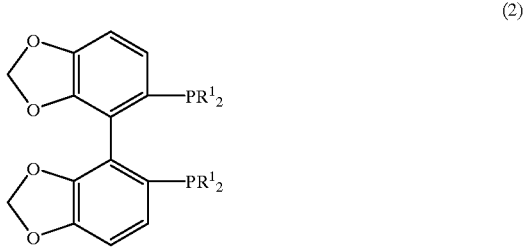

(2)

wherein $R^1$ represents a phenyl group which is optionally substituted with up to three substituents selected from alkyl of 1–4 carbon atoms, alkoxy of 1–4 carbon atoms, methylenedioxy, halogen, trihalomethyl, cycloalkyl of 3–8 carbon atoms, 1-naphthyl and 2-naphthyl, to produce the ruthenium complex of formula (3).

* * * * *